US010854005B2

(12) United States Patent
Lisse et al.

(10) Patent No.: US 10,854,005 B2
(45) Date of Patent: Dec. 1, 2020

(54) VISUALIZATION OF ULTRASOUND IMAGES IN PHYSICAL SPACE

(71) Applicants: Sean A. Lisse, Woodbridge, CT (US); Fabian Max Laage-Gaupp, New Haven, CT (US); Andreas Erben, New Haven, CT (US)

(72) Inventors: Sean A. Lisse, Woodbridge, CT (US); Fabian Max Laage-Gaupp, New Haven, CT (US); Andreas Erben, New Haven, CT (US)

( * ) Notice: Subject to any disclaimer, the term of this patent is extended or adjusted under 35 U.S.C. 154(b) by 161 days.

(21) Appl. No.: 16/122,424

(22) Filed: Sep. 5, 2018

(65) Prior Publication Data

US 2020/0074737 A1 Mar. 5, 2020

(51) Int. Cl.
| | |
|---|---|
| G06K 9/00 | (2006.01) |
| G06T 19/00 | (2011.01) |
| G06T 7/00 | (2017.01) |
| G06T 7/70 | (2017.01) |
| A61B 8/00 | (2006.01) |
| A61B 8/08 | (2006.01) |

(52) U.S. Cl.
CPC .............. *G06T 19/006* (2013.01); *A61B 8/08* (2013.01); *A61B 8/44* (2013.01); *G06T 7/0012* (2013.01); *G06T 7/70* (2017.01)

(58) Field of Classification Search
None
See application file for complete search history.

(56) References Cited

U.S. PATENT DOCUMENTS

| | | |
|---|---|---|
| 2011/0306986 A1 | 12/2011 | Lee et al. |
| 2013/0079627 A1 | 3/2013 | Lee |
| 2016/0191887 A1 | 6/2016 | Casas |
| 2016/0249989 A1* | 9/2016 | Devam .................. A61B 5/021 345/633 |

OTHER PUBLICATIONS

Sato et al., "Image Guidance of Breast Cancer Surgery Using 3D Ultrasound Images and Augmented Reality Visualization", IEEE Transactions on Medical Imaging, vol. 17, No. 5, Oct. 1998, (26 pages).

(Continued)

*Primary Examiner* — Atiba O Fitzpatrick
(74) *Attorney, Agent, or Firm* — Sean E. Serraguard

(57) ABSTRACT

Systems and methods of real-time augmented visualization of anatomical features are disclosed herein. The systems and methods can use concurrently collected and/or preexisting data regarding an anatomical structure to present an image of the anatomical structure to an operator in virtual space as overlayed in real space. The systems and methods can include acquiring image data from an anatomical structure of a subject. Visual image data of the subject can then be received, including non-rigid deformation of the subject. The device pose of the ultrasound device in real space can be determined using device pose data. Image pose of the image data can then be determined in virtual space. Then, a perspective pose of the image of at least a portion of the anatomical structure in virtual space can be mapped to the subject in real space.

20 Claims, 8 Drawing Sheets

(56) References Cited

OTHER PUBLICATIONS

Richardson, "Augmented Reality for Surgery", Retrieved from the Internet: <https://www.mdtmag.com/article/2017/08/augmented-reality-surgery>, Retrieved Apr. 29, 2018, (6 pages).
Imperial College London, "Augmented reality helps surgeons to 'see through' tissue and reconnect blood vessels", Retrieved from the Internet: <https://www.sciencedaily.com/releases/2018/01/180131085837.htm>, Retrieved Apr. 29, 2018, (5 pages).
Alamy, Alamy Stock Photo, Retrieved from the Internet: <www.alamy.com>, Retrieved Apr. 29, 2018, (1 page).

* cited by examiner

VISUALIZATION OF ULTRASOUND IMAGES IN PHYSICAL SPACE

TECHNICAL FIELD

Embodiments described herein generally relate to virtual imaging. More specifically, embodiments generally relate to the use of augmented reality in anatomical visualization.

BACKGROUND

During a surgical procedure, a physician can generally monitor both the subject and a physical screen displaying the subject's anatomical information for guidance in an operation. Using the information provided on the physical screen, the physician correlates the information with the equivalent parts of the patent to understand the location of the target structures. However, this type of mental mapping is difficult, has a steep learning curve, and compromises the accuracy of the information used.

A variety of companies have developed equipment to provide intraoperative interactive surgery planning and display systems, mixing live video of the external surface of the subject with interactive computer-generated models of internal anatomy, as obtained from medical diagnostic imaging data of the subject. The computer images and the live video are coordinated and displayed to a physician during surgery, allowing the physician to view internal and external structures and the relationship between them simultaneously, and adjust the surgery accordingly. These conventional systems may enhance the surface reconstruction or image registration.

SUMMARY

The systems and methods described herein include the use of augmented reality in combination with various imaging techniques, such as ultrasound, for surgical procedures. The anatomical structures can be presented in real-time to the operator, through an augmented reality display, to allow the operator to "see" the anatomical structure as part of the subject before and during the operation. In one embodiment, an anatomical presentation system for real-time augmented visualization of anatomical features is disclosed. The anatomical presentation system can include one or more processors, and a memory communicably coupled to the one or more processors. The memory can store an acquisition module comprising instructions that when executed by the one or more processors cause the one or more processors to acquire image data, using an ultrasound device, from an anatomical structure of a subject, and to receive visual image data of the subject. The visual image data can include non-rigid deformation of the subject. The memory can further store a coordination module comprising instructions that when executed by the one or more processors cause the one or more processors to determine device pose of the ultrasound device in real space, and to determine image pose data of the image data in virtual space, with relation to the ultrasound device, the subject, and an operator in real space. The memory can further store a visualization module comprising instructions that when executed by the one or more processors cause the one or more processors to map a perspective pose of an anatomical structure image in virtual space to the subject in real space.

In another embodiment, a non-transitory computer-readable medium for real-time augmented visualization of anatomical features is disclosed. The computer-readable medium can store instructions that when executed by one or more processors cause the one or more processors to acquire image data, using an ultrasound device, from an anatomical structure of a subject. The computer-readable medium can further store instructions to receive visual image data of the subject, wherein the visual image data can include non-rigid deformation of the subject. The computer-readable medium can further store instructions to determine device pose of the ultrasound device in real space. The computer-readable medium can further store instructions to determine image pose data of the image data in virtual space, in relation to the ultrasound device, the subject, and an operator in real space. The computer-readable medium can further store instructions to map a perspective pose of an image of at least a portion of the anatomical structure in virtual space to the subject in real space.

In another embodiment, a method for real-time augmented visualization of anatomical features is disclosed. The method can include acquiring image data, using an ultrasound device, from an anatomical structure of a subject. The method can further include receiving visual image data of the subject, the visual image data including non-rigid deformation of the subject. The method can further include determining a device pose of the ultrasound device in real space. The method can further include determining image pose data of the image data in virtual space, in relation to the ultrasound device, the subject, and an operator in real space. The method can further include mapping a perspective pose of an image of at least a portion of the anatomical structure in virtual space to the subject in real space.

Embodiments of the present application can be more clearly understood in relation to the figures and the description below.

BRIEF DESCRIPTION OF THE DRAWINGS

So that the manner in which the above recited features of the present disclosure can be understood in detail, a more particular description of the disclosure, briefly summarized above, may be had by reference to the embodiments, some of which are illustrated in the appended drawings. It is to be noted, however, that the appended drawings illustrate only typical embodiments of this disclosure and are therefore not to be considered limiting of its scope. The disclosure may admit to other equally effective embodiments.

To facilitate understanding, identical reference numerals have been used, wherever possible, to designate identical elements that are common to the figures. Additionally, elements of one embodiment may be advantageously adapted for utilization in other embodiments described herein.

DETAILED DESCRIPTION

The systems and methods described herein include the use of augmented reality in combination with various imaging techniques, such as ultrasound, for surgical procedures. The systems and methods described herein include an image acquisition device and an augmented reality display, as integrated through the anatomical presentation system. The anatomical presentation system includes components and modules which can co-ordinate acquisition and proper positioning of the imaging data in order to ease use and understanding. The anatomical presentation system can further include instructions for tracking the probe's location with respect to the operator, the surrounding physical environment, the subject, or combinations thereof. Thus, the image acquisition system is capable of generating an image of a target anatomical structure of the subject, and of showing the acquired image in virtual space, appearing as if in actual space in front of the operator.

The image acquisition system can further repeat a cycle of image acquisition from the probe, determination of the probe's location in space, and projection of the image in front of the operator. In this way, the anatomical presentation system may project the image in real-time so that it appears to overlap the imaged anatomy in real space, when appropriate. In further embodiments, the anatomical presentation system can capture information about the physical environment, the probe's location, and the imaging data, in order to better communicate and store the orientation of the imaging subject and the probe with relation to the acquired imaging data. Embodiments of the present application can be more clearly understood in relation to the figures and the description below.

Figure 1A:
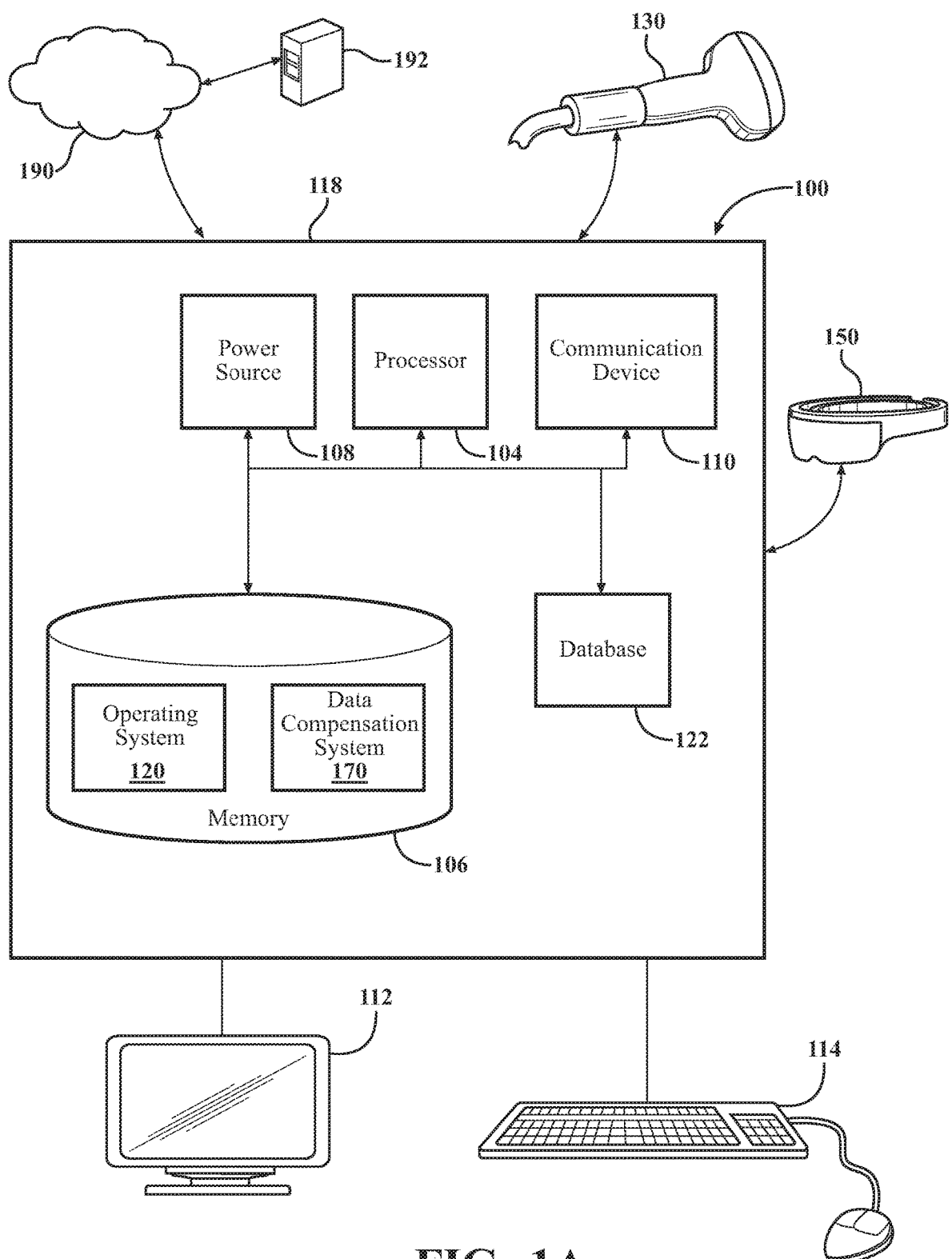
FIGS. 1A-1C are illustrations of device components adaptable for use with an anatomical presentation system, according to embodiments described herein.
Figure 1B:
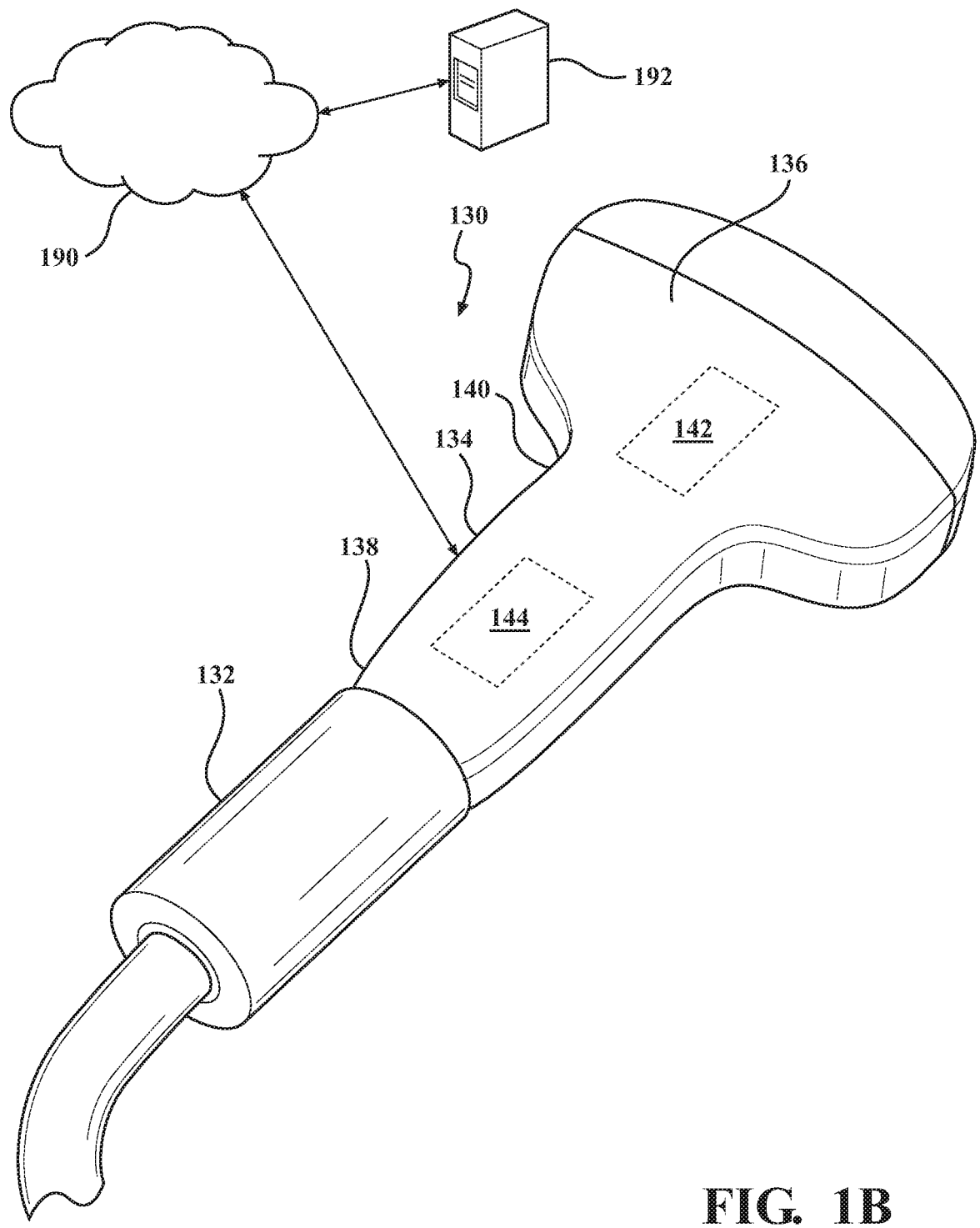
Figure 1C:
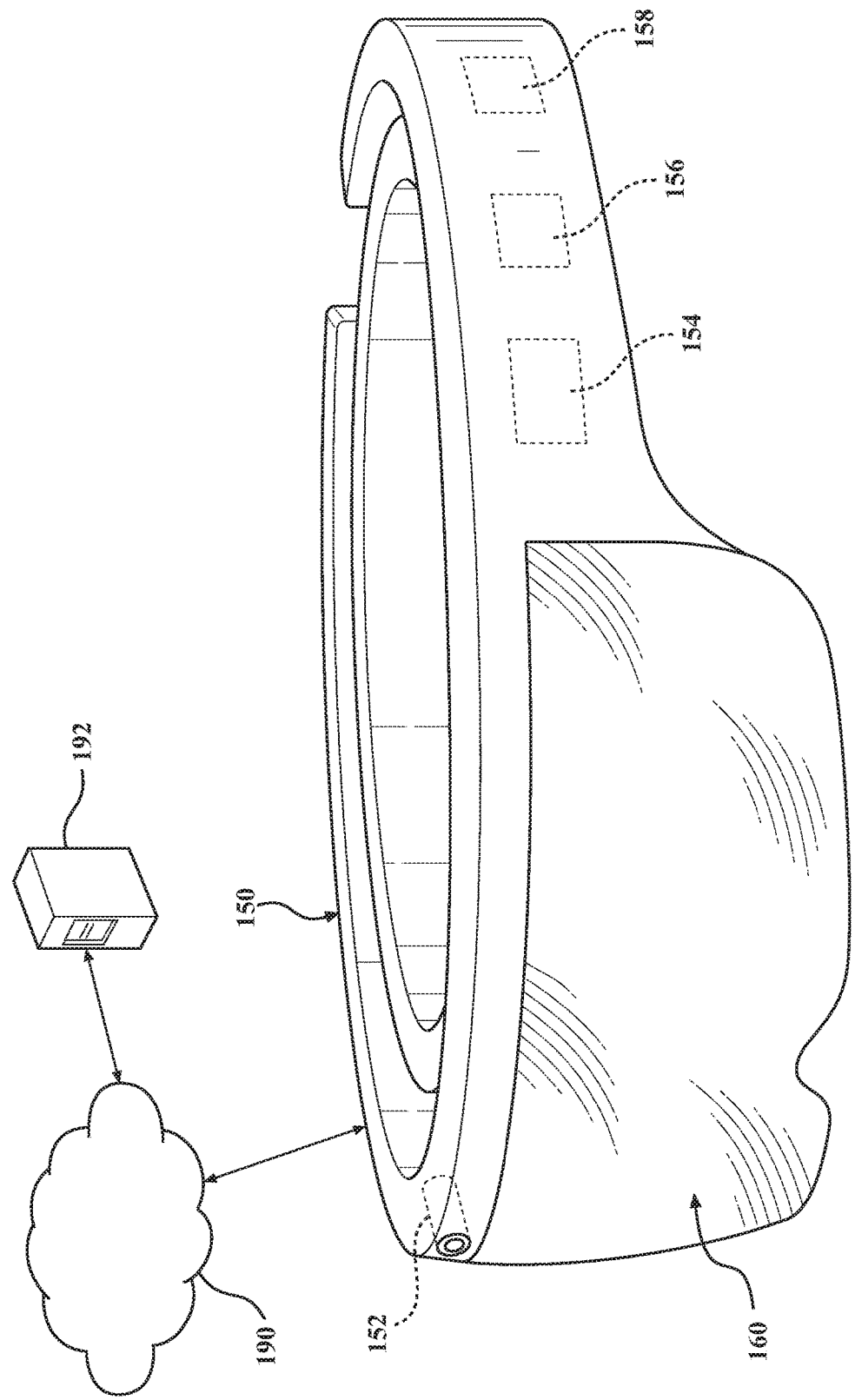

Referring to FIGS. 1A, 1B, and 1C, an example of device components adaptable for use with an anatomical presentation system 170 is illustrated. The device components, as used herein, can include a computing device 100, an ultrasound device 130 and an augmented reality (AR) display device 150. The computing device 100, as shown in FIG. 1, can be any appropriate type of computing device such as, but not limited to, a personal computer (PC), workstation, embedded computer, or stand-alone device with a computational unit, such as a microprocessor, digital signal processor (DSP), field programmable gate array (FPGA), or application specific integrated circuit (ASIC). Shown here, the computing device 100 is an embedded computer. While arrangements for computing devices 100 will be described herein with respect to an embedded computer, it will be understood that embodiments are not limited to embedded computers. In some embodiments, the computing device 100 can be any other form of computing device that, for example, can operate at least semi-autonomously, includes object detection or the capability to support object detection, and thus benefits from the functionality discussed herein.

The computing device 100 is primarily depicted in FIG. 1A. Shown here, the computing device 100 can communicate directly or indirectly with the ultrasound device 130 and the AR display device 150. The computing device 100 can contain various components for performing the functions that are assigned to said computing device. The components can include a processor 104, like a central processing unit (CPU), a memory 106, a power source 108, communications device 110, input and/or output devices, which can optionally include a monitor 112, a keyboard, and/or mouse 114, and at least one bus 116 that connects the aforementioned components. In some embodiments, these components are at least partially housed within a housing 118.

The processor 104, which can also be referred to as a CPU, can be a device which is capable of receiving and executing one or more instructions to perform a task as part of a computing device. In one embodiment, the processor 104 can include a microprocessor such as an application specific instruction set processor (ASIP), graphics processing unit (GPU), a physics processing unit (PPU), a DSP, an image processor, a co-processor, or others. Though referenced as the processor 104, it is understood that one or more processors 104 can be used in one or more embodiments described herein, including combinations of processors 104.

The memory 106 is any piece of hardware that is capable of storing data or information. Examples of data or information which can be stored in the memory 106 include, without limitation, data, program code in functional form, and/or other suitable information either on a temporary basis and/or a permanent basis. The memory 106 can include one or more modules that include computer-readable instructions that, when executed by the processor 104, cause the processor 104 to perform methods and functions that are discussed herein. The memory 106 can include volatile and/or non-volatile memory. The memory 106 can further include a computer-readable storage medium. Examples of suitable memory 106 include RAM (Random Access Memory), flash memory, ROM (Read-Only Memory), PROM (Programmable Read-Only Memory), EPROM (Erasable Programmable Read-Only Memory), EEPROM (Electrically Erasable Programmable Read-Only Memory), registers, magnetic disks, optical disks, hard drives, or any other suitable storage medium, or any combination thereof.

The memory 106 can be a component of the processor(s) 104, or the memory 106 can be operably connected to the processor(s) 104 for use thereby. The memory 106 can include an operating system 120, such as LINUX. The operating system 120 can include batch, live, time sharing, real-time, and other types of operating systems. The operating system 120, as described herein, can include instructions for processing, accessing, writing, storing, searching data, or other functions as selected by the operator for controlling and providing an interface with the computing device 100. As used herein, the operator can be a physician, a technician, or a third party applying one or more components of the embodiments described herein. The memory 106 can include communications procedures for communicating with the network 190, another computing device, and/or a server.

The communication device 110 can be wired or wireless connection components and/or software allowing the computing device 100 to communicate with other computing devices. The communication device 110 can allow communication with devices either locally or remotely, such as over a network protocol (e.g., Ethernet or similar protocols). In one example, the computing device 100 is connected to the network 190 using the communication device 110. The communication device 110 can further be connected with remote devices associated with other computing devices. In one example, the communication device 110 of the computing device 100 is connected with the ultrasound device 130 through the network 190. In further embodiments, the computing device 100 can connect with a second server, allowing access to real-time image data from secondary ultrasound devices, which are connected to or in connection with the server 192. The secondary ultrasound devices can include one or more ultrasound devices which are substantially similar to the ultrasound device 130, described with reference to FIG. 1.

The computing device 100 can further include the anatomical presentation system 170 or components thereof. As described herein, certain components of the anatomical presentation system 170 can be stored locally in the computing device 100, in the computing device 100 at a remote location, such as a server, or in combinations thereof. As such, one or more embodiments of the anatomical presentation system 170 can include the anatomical presentation system 170, modules thereof, or components thereof as being stored, collected, created, compared or otherwise made available from the memory 106 or the database 122 of the computing device 100. When stored as part of the computing device 100, the anatomical presentation system 170 can access the computing device 100, another computing device 100, one or more sensors, or other devices through the communications device 110 and the network 190, allowing for continuity between the one or more components which comprise the anatomical presentation system 170, as disclosed herein.

The ultrasound device 130 is discussed in greater detail, in FIG. 1B. The ultrasound device 130 can be in communication with the computing device 100, such as through the network 190. The ultrasound device 130 can include a handle 132, a shaft 134, and an ultrasonic head 136, as schematically illustrated in FIG. 1. The ultrasound device 130 can include the ultrasonic head 136 attached on a first end 140 of the shaft 134 and the handle 132 attached on a second end 138 of the shaft 134. The ultrasonic head 136 can contain, depending on the use, one or more transducer elements 142 for sending or receiving ultrasonic waves. The ultrasonic head 136 can be arranged for generation of uniplanar or biplanar real-time ultrasonic, Doppler, color Doppler, 3D-ultrasonic images, or other forms of ultrasonic or hybrid ultrasonic images. The shaft 134 serves to connect the handle 132 and the ultrasonic head 136. The shaft 134 can include a flexible or rigid material, depending on the use. The shaft 134 can further store one or more electronic components 144, which can be used in generating, capturing, storing, and/or transferring ultrasound data.

Data produced by the ultrasound device 130, as well as data produced by other imaging devices, can be referred to as real-time image data. Real-time image data is image data produced in a similar time frame to and in sync with the time of use. As such, real-time image data allows for constant update to imaging and production of new images as the anatomical structure changes. In this example, the ultrasound device 130 produces real-time image data which can be incorporated into the anatomical presentation system 170 to produce the anatomical structure images described herein. An example of an ultrasound device, which can be implemented as the ultrasound device 130 and modified for use with the embodiments described herein is a PC-enabled ultrasound device by TELEMED®. Other sources of ultrasound data, including sources which are composed of multiple components or use different shapes or sizes can be incorporated or modified for use with the embodiments described herein.

The AR display device 150 is further disclosed in FIG. 1C. The AR display device 150 is a device which allows an operator to view a real space with one or more electronic images (e.g., virtual objects) in virtual space overlaid onto the real space. More specifically, with reference to FIG. 1, the augmenting image (the image of the virtual object projected from virtual space onto real space) is perceived by the operator through or in the AR display device 150 which is intended to comprise any type of headset through or in which an electronic image can be displayed to the wearer.

The AR display device 150 presents a virtual space overlaid onto a real space. The real space, as used herein, is the three (3) dimensional space physically occupied by real world objects, such as the subject, surgical tools and the operator. The virtual space, as used herein, is an equivalent three (3) dimensional space, or portion thereof, generated by one or more computing devices, which is occupied by one or more virtual objects. An example of an AR display device, which can be implemented as the AR display device 150 and modified for use with the embodiments described herein is a HoloLens head-mounted display by MICROSOFT®.

An image capture device 152 can capture the normal real space field of view of the operator of the AR display device 150, where normal refers to a field of view (overall view range as well as eye level and position) which feels natural to a human observer. As such, the image capture device 152 can be mounted on the headset in a manner to give the operator the comfortable impression that the image he perceives is substantially similar to the one he would see when not wearing the AR display device 150. Embodiments which can be used as the AR display device 150 include head-mounted displays, completely immersive displays, and "heads-up" displays (displays which superimpose the electronic display over a view of real space). The image capture device 152 can provide the computing device 100 with the same view that the operator sees, allowing the electronic image to be displayed to allow for comfortable and convenient interaction between a real reference object (e.g., a subject), within the field of view of the operator.

The AR display device 150 can further include a video display 160. The video display 160 may be any type of display such as an LCD screen, electroluminescent screen, an OLED screen, and the like. In one embodiment, the video display 160 may include a gesture responsive screen. The gesture responsive screen may be used to allow the operator to provide input data while viewing AR video. For example, an operator may add a label identifying each tool on the screen for the physician. In further embodiments, the operator can modify or interact with one or more images which are presented on the video display 160. Possible modifications and interactions include modifications to the anatomical structure image, as described further with reference to FIG. 2. In another embodiment, one or more AR display devices 150 can be employed. Thus allowing the images to be presented to one or more operators respectively and allowing accompanying perspectives and interactions, as described in embodiments herein.

The video capture component 154 includes electronic elements that can convert the signal from the image capture device 152 into perspective data. The perspective data can be stored in the computing device 100. The video capture component 154 outputs the perspective data to the computing device 100. The perspective data can be a digitized and processible representation of what the operator sees from the field of view of the image capture device 152. The video generation component 156 takes image values from the environmental information, as received by the computing device 100, and converts them into a viewable format that can be displayed on the video display 160 of the AR display device 150. The signal generated by the image capture device 152 can be different from the signal displayed on the AR display device 150 by the addition of the computer-generated image to thereby form a synthetic image as an augmented reality display. The computer-generated image can be produced, in part, using data derived from the ultrasound device 130. The above components can be in communication with the AR display device 150 through a number of mechanisms, such as incorporated as part of the computing device 100, stored as part of the AR display device 150, stored as part of a server (such as the server 192), or combinations thereof. The server can be substantially similar to the computing device 100. In further embodiments, the server can include one or more of the components described with reference to the computing device 100, including the memory 106, the processor 104, the power source 108 and others.

Figure 2:
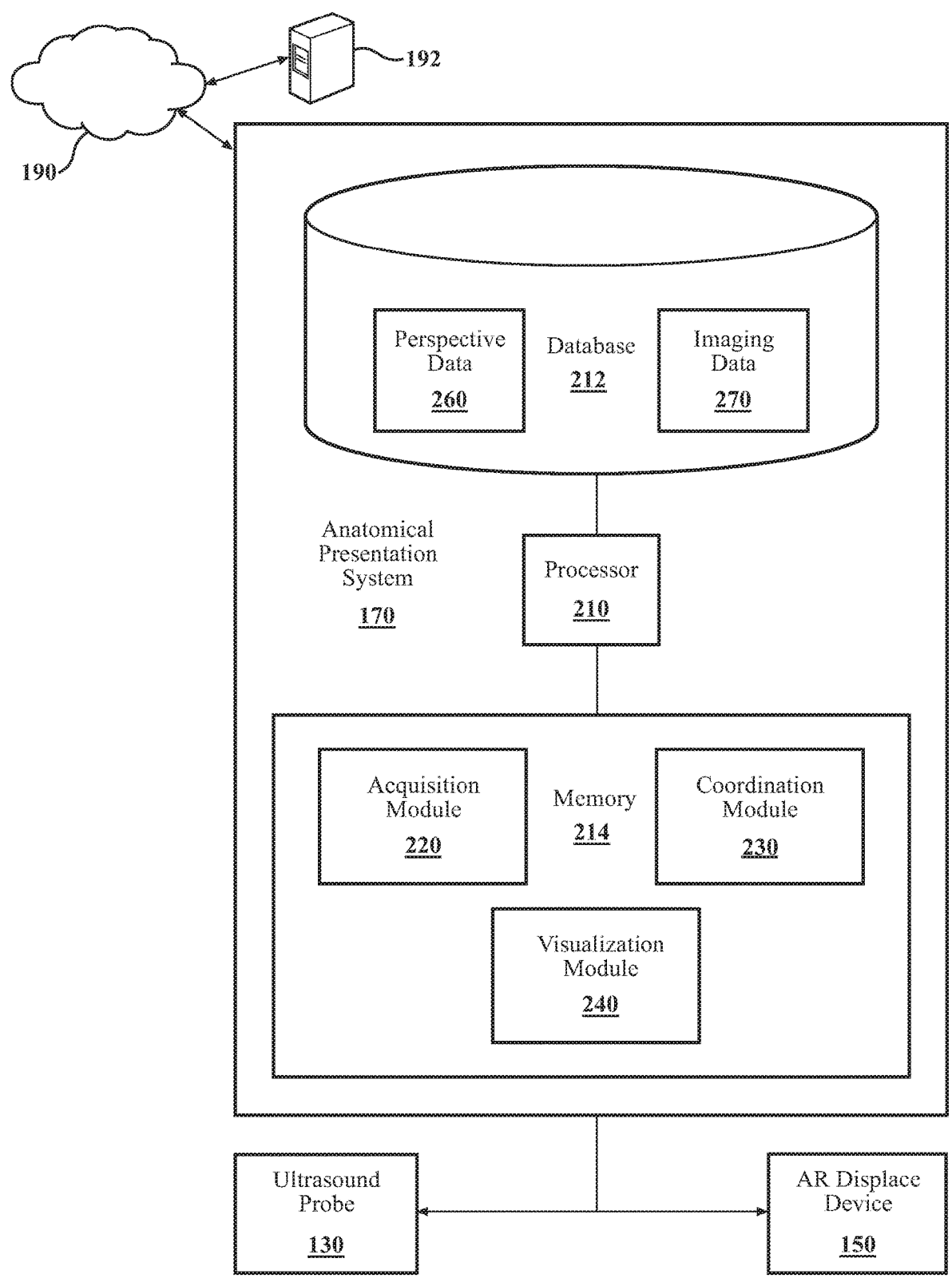
FIG. 2 is an illustration of an anatomical presentation system for real-time augmented visualization of anatomical features, according to embodiments described herein.

The discussion of the anatomical presentation system 170 begins at FIG. 2, with an illustration of the anatomical presentation system 170, according to one embodiment. The anatomical presentation system 170 is shown as including a processor 210. The processor 210 can be the processor 104 from the computing device 100, depicted in FIG. 1, a substantially similar processor, or a different processor. Accordingly, the processor 210 can be a part of the anatomical presentation system 170, the anatomical presentation system 170 can include the processor 210 as separate from the processor 104, or the anatomical presentation system 170 can access the processor 104 through a data bus or another communication path. Though described herein as the processor 210, it is understood that the processor 210 can include one or more processors and/or combinations of processors of various types, including any or all of those described herein.

In one embodiment, the anatomical presentation system 170 includes the memory 214 that stores an acquisition module 220, a coordination module 230 and a visualization module 240. The memory 214 can be a RAM, ROM, a hard disk drive, a flash memory, or other suitable memory for storing the modules 220, 230, and 240. The modules 220, 230, and 240 are, for example, computer-readable instructions that when executed by the processor 210, cause the processor 210 to perform the various functions disclosed herein.

The anatomical presentation system 170 can further include a database 212. The database 212 can be presented in a number of configurations, including as part of the memory 214, as an independent component from the memory 214, as part of a separate memory (distinct from memory 214), or others. The database 212 can include perspective data 260 and imaging data 270. The perspective data 260 can include data and information regarding the environment from the point of view of the operator, such as information as detected by the image capture device 152. The perspective data 260 can include data from secondary capture devices, as adapted for the point of view of the operator. The perspective data 260 can be transmitted through a network 190 from a server 192, such as data collected at different points in time or from different sensors. The imaging data 270 can include information related to an anatomical imaging device, such as the ultrasound device 130, described with reference to FIG. 1. Though the anatomical presentation system 170 is described with reference to the computing device 100, the anatomical presentation system 170 or portions thereof, can be stored in separate components (e.g., the ultrasound device 130 and/or the AR display device 150), on a computing device, such as the server 192, or others. As such, one or more of the functions of the anatomical presentation system 170 or the modules contained therein, can be performed remotely and transferred to computing device 100 as part of the embodiments described herein.

The anatomical presentation system 170 is configured to store imaging data transmitted to AR display device 150 by at least the ultrasound device 130 as well as process and analyze the imaging data. The ultrasound device 130 can be a handheld device (e.g., a handheld ultrasound device), a laparoscopic tool, a robotic tool, or others capable of emitting and receiving ultrasonic waves and interpreting said waves into imaging data. The anatomical presentation system 170 can also be connected to other devices, such as a server, such as a server 192, and the AR display device 150. The computing device 100 may be used for processing output data generated by the AR display device 150 for output on the AR display device 150. Additionally, the computing device 100 can receive a real-time video signal from the image capture device 152, as attached to the AR display device 150. The computing device 100 can further be used for additional processing of the pre-operative imaged data. In one embodiment, the results of pre-operative imaging such as an ultrasound, magnetic resonance imaging (MRI), x-ray, or other diagnosing image may be stored internally, as part of the imaging data 270, for later retrieval by the computing device 100.

The anatomical presentation system 170 can begin at the acquisition module 220. The acquisition module 220 can include instructions that, when executed by the processor 210, cause the processor to acquire an image data set, using an ultrasound device, from an anatomical structure of a subject. The operator applies the ultrasound device 130 to the subject. The one or more transducer elements then produce ultrasound and receive reflected ultrasound, producing an image data set for the anatomical structure that is targeted by the ultrasound device 130. In one or more embodiments, the ultrasound device is moved by the operator or another party across the target surface of the subject, such that image data set is received from a variety of angles.

The imaging data 270 can include data that describes the position and orientation of the anatomical structure in three (3) dimensional space, commonly referred to as pose. The pose of the anatomical structure can be established in relation to a reference frame, thus establishing at least a portion of the orientation and boundaries applied to the virtual space. The reference frame can include other real space objects, such as other anatomical structures or environmental objects. The acquisition module 220 collects data related to the anatomical structure and stores the image data set as part of the imaging data 270. The imaging data 270 can then be stored in the database 212. The image data set can include externally and internally derived data sets, such as ultrasound delivered through the skin, through one or more bodily openings, laparoscopically, or others.

The image data set can further comprise data that has been collected over a period of time. In one embodiment, the image data set can include ultrasound imaging data which has been collected over a variety of subject visits with the operator. In another embodiment, the imaging data 270 can include secondary imaging data, the secondary imaging data being derived from one or more secondary detection events. Secondary detection events can include the use of one or more imaging devices for the production of imaging data 270 regarding one or more anatomical structures. Examples of secondary detection events can include data which has been collected by a variety of different providers, data which has been collected by at a variety of times, imaging data from secondary imaging techniques, or combinations thereof. Secondary imaging techniques can include techniques which can be used or modified for imaging one or more anatomical structures, such as MRI, x-ray radiography (including computerized axial tomography), elastography, thermography, and others. The image data set can be collected with source agnostic information, such that information from different source sensors can be combined or used to augment the imaging data 270. The source agnostic information can include information regarding physical parameters which are determined from the measurements (e.g., temperature, physical dimensions, tensile strength, proximity to other anatomical structures, movement rates, presence or absence of obstructions, and others). The imaging data about the anatomical structure from the variety of time frames and origins can be oriented to one another using common points in virtual space to create a model of the anatomical structure.

The acquisition module 220 can further include instructions to receive visual image data of the subject, the visual image data including non-rigid deformation of the subject. The visual image data of the subject is one or more sources of external imaging of the subject. The visual image data includes information regarding the general shape, orientation and position of the subject such that the anatomical structure can be properly associated with the position of the subject. The visual image data can include reference information, such as the pose of objects in the environment. The visual image data can include still frame or video imaging received by one or more image capture devices, such as the image capture device 152. In one embodiment, the visual image data further includes data collected from a remote source, such as one or more image capture devices positioned as part of infrastructure, such as on a wall in an operating room.

The visual image data can further include information regarding non-rigid deformation. Non-rigid deformation generally relates to the mobility of the tissue, in response to one or more forces applied to the tissue. The non-rigid deformation can be movement of the skin and organs in response to pressure, such as applied by an operator through the ultrasound device. The non-rigid deformation of the anatomical structure can provide information regarding the present and original positions of the anatomical structure. Further, the non-rigid deformation can provide information regarding the elasticity of the anatomical structure, related rigid or non-rigid structures, the permanency of the non-rigid deformation, or others. The visual image data can be stored as part of the imaging data 270, as shown in the database 212. In further embodiments, the visual image data can be stored or accumulated remotely, such as when transferred through a network 190 to a server 192.

In further embodiments, the acquisition module 220 can further include instructions to receive or collect tissue deformation data about the subject, using one or more secondary detection devices. The one or more secondary devices can be devices capable of collecting information regarding non-rigid deformation of an anatomical structure. The one or more secondary devices can include MRI devices, computed tomography (CT) devices, and other capable of producing tissue deformation data. The tissue deformation data can be data from a variety of sources related to non-rigid deformation of an anatomical structure. The tissue deformation data can be stored as part of the imaging data 270, as shown in the database 212. In further embodiments, the tissue deformation data can be stored or accumulated remotely, such as when transferred through a network 190 to a server 192.

In further embodiments, the non-rigid deformation of the anatomical structure can provide information regarding possible future positions and deformations of the anatomical structure. Without intending to be bound by theory, the non-rigid deformation of the anatomical structure, in the absence of severe trauma, is expected to be reproducible. As such, the acquisition module 220 can include instructions to apply that expected reproducibility to determine where and how an anatomical structure will move when a force is applied. Here, the forces applied, including quantity, origin and direction of the force, can be used to determine where and how the anatomical structure will move when force is applied again. Thus, the level of non-rigid deformation or displacement of the anatomical structure can be related to an applied force for the purposes of future prediction. The imaging data 270, including the image data set and the visual image data, can then be transmitted, presented or made available to the coordination module 230.

The coordination module 230 can include instructions that, when executed by the processor 210, cause the processor to determine device pose using device pose data of the ultrasound device 130 in real space. The device pose data is information regarding the real space pose of the ultrasound device. The device pose, as used herein, is described in the sense of six degrees of freedom. As such, the device pose involves the position and orientation of the device with respect to a reference object or the environment generally. Device pose is measurement of the device both regarding position on the three (3) dimensional plane (X, Y, and Z-axes) and rotational position as compared to normal on each of those axes. The movement, as used herein, in light of six degrees of freedom, includes both translation and rotation in relation to a three dimensional plane. Translation and rotation can be described with reference to the reference object having a known starting position and direction, left or right (referred to as "sway"), up or down (referred to as "heave"), and movement backwards and forwards (referred to as "surge"), corresponds to movement on X, Y, and Z planes respectively. Pitch is rotation about the X plane. Yaw is rotation about the Y plane. Roll is rotation about the Z plane.

The device pose data can be determined based on external information sources, internal information sources, or combinations thereof. Internal information sources can include information from sources which are connect to or connected with the ultrasound device, such as derived from a gyroscope, an accelerometer, a magnetometer, a geolocation device (e.g., GPS, WiFi-based localization system), or others. In one embodiment internal information, the device pose data can be determined based on a magnetometer located within the ultrasound device. External information can include information from sources outside of or external to the ultrasound device 130. In one embodiment of external information, device pose data is determined based on one or more images produced by image capture devices, the image capture devices being positioned in known locations in the environment. Once determined, the device pose data can be stored as part of the perspective data 260 in the database 212.

The coordination module 230 can further include instructions to determine image pose data of the image data set. The image pose data is information regarding the pose of the image of the anatomical structure in virtual space. Since the virtual space reflects and is superimposed over real space, the image pose data will reflect the real space position of the anatomical structure. In one or more embodiments, the image pose data can be determined using the position and/or pose data from environmental objects, such as the device pose data described above with reference of the ultrasound device. In further embodiments, the image pose data is determined at least in part based on the pose of the subject. The image pose data can include translations, positional, rotational data regarding the anatomical structure. Further, the image pose data can include information regarding the non-rigid deformation of the anatomical structure, either as detected or as anticipated based on predictive information described above. The image pose data can include data derived from multiple sources, such as previous data collected regarding the anatomical structure, accumulated data regarding equivalent anatomical structures in other subjects, or others. The image pose data can then be stored as part of the perspective data 260, as shown in the database 212.

In further embodiments, the coordination module 230 can further include instructions to determine operator perspective. The operator perspective can be determined from a variety of sources, such as the operator eye position, the position of the image capture device on the AR display device 150, or others. In one embodiment, the operator eye position can be used to determine the perspective of the operator. The operator eye position can be determined by a variety of techniques, including one or more image capture devices directed at the eyes. The operator eye position can include determination of gaze, depth perception of the operator, or other factors that can affect the operator's ability to view one or more objects. The operator eye position can be continuously determined, such that changes in the position of the AR display device 150 are accounted for and the presentation of one or more images is not affected. The operator eye position can then be stored as part of the perspective data 260, as shown in the database 212.

The visualization module 240 can include instructions that, when executed by the processor 210, cause the processor to map a perspective pose of an anatomical structure image in virtual space to the subject in real space. The anatomical structure image, as presented to the operator in virtual space, can be overlaid onto the anatomical structure, as it exists in the subject in real space. In one embodiment, the anatomical structure image can be used to show otherwise obstructed angles of the anatomical structure. In another embodiment, the anatomical structure image can include cutaway images of adjacent or occluding anatomical structures, to orient the operator with regards to positioning of the anatomical structure in the subject.

The operator perspective can then be applied by the visualization module 240 to determine the perspective pose of image of the anatomical structure. Using the image pose data, the device pose data, the operator perspective, and other positioning data, the visualization module 240 can provide the operator an image of the anatomical structure with a perspective pose of the anatomical structure. The perspective pose is the presentation of the image of the anatomical structure in the pose of the anatomical structure, as it exists in the subject, from the perspective of the operator. In one or more embodiments, the perspective pose can change, in real-time, with the perspective of the operator. The visualization module 240 can receive updated information on the operator perspective through the coordination module 230. The imaging data 270, including the image data set, can then be accessed to provide the perspective pose of the anatomical structure as it changes over a period of time.

The imaging data 270 can include two dimensional and three dimensional imaging data regarding one or more perspectives of the anatomical structure. The two dimensional and three dimensional imaging data can include data as received from the ultrasound device or other imaging devices. In one embodiment, the imaging data 270 can further include a representative model. In one embodiment, the image data set is applied to modify the representative model of the anatomical structure. The imaging data 270 can be used to create the base framework of the representative model. As the image data set includes the imaging data collected in the current instance by the ultrasound device 130, the image data set can then be applied to modify the representative model in real-time. The representative model can be derived from a variety of model sources. Model sources can include previously identified shapes for known anatomical structures (e.g., general heart or kidney shape) or previously identified shapes as modified by diseases states and known subject anomalies (e.g., a general heart shape for a person with left ventricular hypertrophy). Model sources can further include geometric primitives with or without modification by imaging data. As such, the imaging data 270, including the image data set, can be applied to create or update the representative model source for one or more anatomical structures. Various data incorporation techniques can be used to incorporate the imaging data 270 to produce the representative model, such as Bayesian filtering, feature detection and fitting, spatiotemporal 3D reconstruction, or others.

The visualization module 240 can be configured to analyze the image data set to recognize the anatomical structure. The analysis can include instructions to monitor for one or more anatomical structures in the subject and compare to existing models. In this way, the anatomical structure can be uniquely identified and differentiated from other anatomical structures. This unique identification is converted to recognition data, which can be stored, processed or otherwise maintained. Once anatomical structure is uniquely identified, the anatomical structure can be associated with a representative model having a unique identifier. The unique identifier can be preexisting, such as when the anatomical structure has been detected before, or the unique identifier can be created in response to a new anatomical structure. The unique identifier can be stored along with one or more 3D objects or representative models which can be associated with the anatomical structure. If an anatomical structure is detected that has already received a unique identifier, the anatomical structure can then be associated to a preexisting representative model. The data as described here can be further manually associated to a subject through user input. One or more data points from the image data set can be incorporated into the model, such that the representative model better reflects the anatomical structure.

In another embodiment, the model sources can be personalized to a specific subject. As differentiated from a subject specific presentation of the anatomical structure, using more general models for adaptation, subject models can be generated that specifically address the subject's unique physiology at one or more anatomical structures. In embodiments described herein, imaging data can be collected from a variety of points of view over a period of time. This imaging data can be applied to modify or create a subject specific 3D model, unique to the physiology of the subject. The subject specific model can then be referenced during scanning, modified using the image data set, and presented to the operator during a procedure. In this way, the models sources will require less real-time modification while providing a high level of detail both on structures that can be currently visualized and those that are not visible based on the current ultrasound placement.

In further embodiments, the visualization module 240 can include instructions to incorporate modification of the anatomical structure image based on one or more actions of the operator in real space. Modifications of the anatomical structure image can include incorporation of surgical procedures as they are performed. In one example, an incision in the anatomical structure by the operator can be detected and depicted in real-time in the anatomical structure image in virtual space. In another embodiment, the modifications can include incorporation of one or more gestures, such as one or more hand movements or audible commands which manipulate the view or pose of the anatomical structure image. In further embodiments, the anatomical structure image can be adjusted based on detected eye position and focus of the operator. Additionally, the modifications can include creating safety boundaries around delicate structures, such as an artery or organ. Further, the visualization module 240 can decipher the one or more pre-operative images to define and label structures, organs, anatomical geometries, vessels, tissue planes, orientation, and other similar information.

In embodiments which include multiple operators, the anatomical presentation system 170 can determine and present multiple perspective poses of the anatomical structure image. In one embodiment, the coordination module 230 can determine the operator perspective for each of the one or more operators. The operator perspective can then be applied to determine the perspective pose of the anatomical structure image for each operator. The visualization module 240 can then include instructions to present the perspective pose of the anatomical structure image to the one or more operators in real-time. In further embodiments, the one or more operators can interact with the anatomical structure or the anatomical structure image and this interaction can be shared with the other operators as part of their respective anatomical structure image, as overlaid on the subject.

In yet further embodiments, the visualization module 240 can render one or more obstructions transparent or invisible to the operator. The visualization module 240 can include instructions to exclude or render transparent objects which are not part of the operator's desired view, including other parties in the operating room, or tools in use by those parties. In this embodiment, the coordination module 230 can include instructions to recognize the one or more object in the operating room. The object recognition can be accomplished using comparison to 3D models, appearance based methods, feature based methods, genetic algorithms, or others. The recognized objects can then be associated by the coordination module 230 to one or more parties.

The visualization module 240 can include instructions to present an image overlay, in virtual space, of the space behind the object, to create the illusion of object transparency or object invisibility for the operator. The visualization module 240 can compare images taken over a period of time to collect data about the operator's view of the room both with the object (the "object view") and without the object (the "displaced view"). The portions of the displaced view can then be blended or overlayed with the object from the object view, thus rendering the object translucent, transparent, or invisible from the perspective of the operator. The image overlay can be updated in real-time such that the image follows the object or the person.

In further embodiments, the anatomical presentation system 170 can include instructions to track and/or recognize surgical instruments or other devices in real space, such as for virtual representation. The anatomical presentation system 170 can track and recognize surgical instruments or other medical devices in real space. The anatomical presentation system 170 can then generate a virtual representation of them that can be fused with the imaging data. The virtual representation can be applied by the anatomical presentation system 170 to display the interaction of the surgical instruments or other devices with further devices present in real space or virtual space. In one embodiment, the virtual representations can be used for training or guidance, such as in a simulated practice environment. In further embodiments, the virtual representation can be linked to the actions of an operator, such as a temporal link. Here, a second user or a first user at a second point in time can have their actions guided by a first user at a first point in time based on the visual representation.

In further embodiments, the anatomical presentation system 170 can include instructions to incorporate imaging information from non-ultrasound sources. The system 170 can include receiving information from a non-ultrasound imaging source. Examples of non-ultrasound imaging sources which can be adapted for use with implementations described herein can include an x-ray imaging device. The data derived from the non-ultrasound imaging source can be used independently or in conjunction with the ultrasound data described herein. The system 170 can further include determining device pose of the non-ultrasound imaging source. The non-ultrasound imaging source can be a stationary device or a mobile device. The device pose can be determined in a substantially similar manner to the ultrasound device, as described herein.

Figure 3:
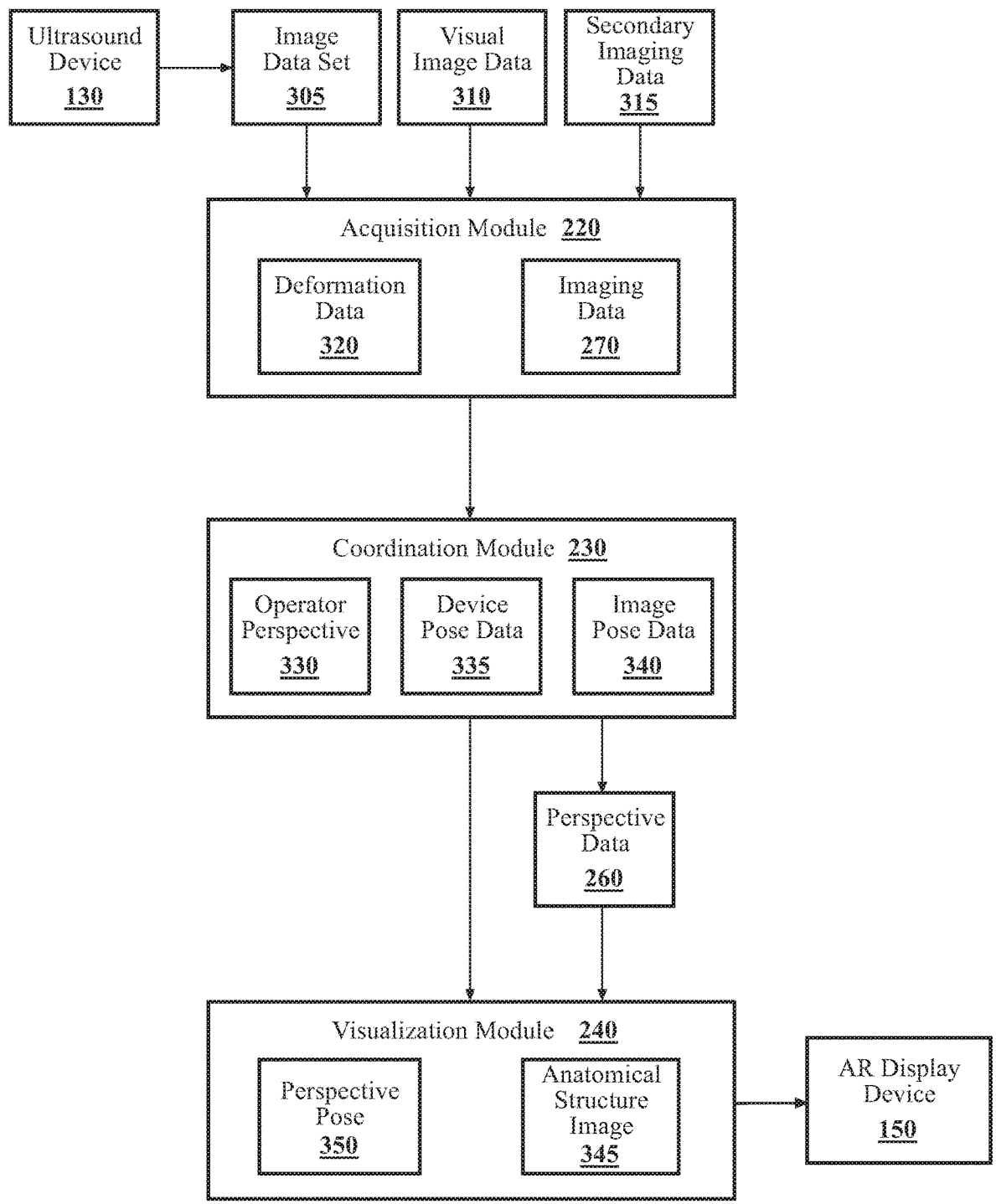
FIG. 3 depicts a schematic diagram of the anatomical presentation system, according to embodiments described herein.

FIG. 3 depicts a schematic diagram of the anatomical presentation system 170, according to embodiments described herein. The anatomical presentation system 170 uses imaging data 270, as derived from at least an ultrasound device, and perspective data 260 to present an AR view of a 3D image of the anatomical structure to an operator. The perspective data 260 can include device pose data and operator perspective data. The anatomical presentation system 170 can incorporate the imaging data 270 and the perspective data 260 to create a 3D image of the anatomical structure. One or more operators can then receive the anatomical structure image, such as during a surgical procedure, to enhance visualization and present a real-life like overlay of the anatomical structure in virtual space.

The anatomical presentation system 170 begins at the acquisition module 220. The acquisition module 220 can include instructions to receive the image data set 305. The image data set 305 can include image data concurrently collected using an ultrasound device. The image data set 305 can be stored as part of the imaging data 270. The imaging data 270 can include data previously collected about the anatomical structure from either the current ultrasound device or secondary imaging data 315, information about the anatomical structure or related structures, information collected over a period of time, and others. The acquisition module 220 can further collect visual image data 310. The visual image data 310 can be used to orient the image data with regards to the environment, the subject, and the anatomical structure. The acquisition module 220 can incorporate the image data set 305, the visual image data 310 and the secondary image data 315 into the imaging data 270. Further, the acquisition module can use the image data set and the visual image data 310 to determine the deformation data 320. The deformation data is a culmination of the non-rigid deformation information regarding at least the anatomical structure.

The imaging data 270 and the deformation data 320 can be forwarded to the coordination module 230 for further data correlation and processing. The coordination module 230 can include instructions to determine the operator perspective 330. The operator perspective 330 can be determined as described above, including based on image capture device perspective, operator gaze, or others. The coordination module 230 can further determine the device pose, by collecting device pose data 335. The device pose data 335 can include information on the position of the ultrasound device 130 during the collection of the image data set 305. The image pose data 340 can then be extrapolated using the device pose data 335 and the operator perspective 330. The image pose data 340 is the desired pose of the anatomical structure image from the operator perspective 330. The operator perspective 330, the device pose data 335 and the image pose data 340 can then be stored as part of the perspective data 260.

The visualization module 240 can then receive the imaging data 270 and the perspective data 260 to produce the anatomical structure image 345. The anatomical structure image 345 is associated with a perspective pose 350 for the operator. The perspective pose 350 is the position and orientation of the anatomical structure image 345 that matches the view of the real space anatomical structure position and orientation from the perspective of the operator. The anatomical structure image 345 can be displayed to the operator through the AR display device 150. Further, the visualization module 240 can include instructions to adjust the anatomical structure image 345 and the perspective pose 350 in real-time for one or more operators, according to one or more embodiments described above.

Thus, the anatomical presentation system 170, through augmentation of the operator view of the anatomical structures in question, can provide numerous benefits to the operator. By providing direct visualization of the anatomical structure, the operator can make a more informed decision about performing one or more procedures. Further, the ability to directly visualize the anatomical structure, rather than through a screen, allows for increased safety for the subject and improved concentration for the operator. Further, the ability to directly visualize the anatomical structure in its relation to the subject's surface anatomy can aid in diagnosis and understanding of pathology or anatomical variants. Finally, the anatomical structure image can incorporate information from previous data collection, this providing information not available from current screen based systems.

Figure 4A:
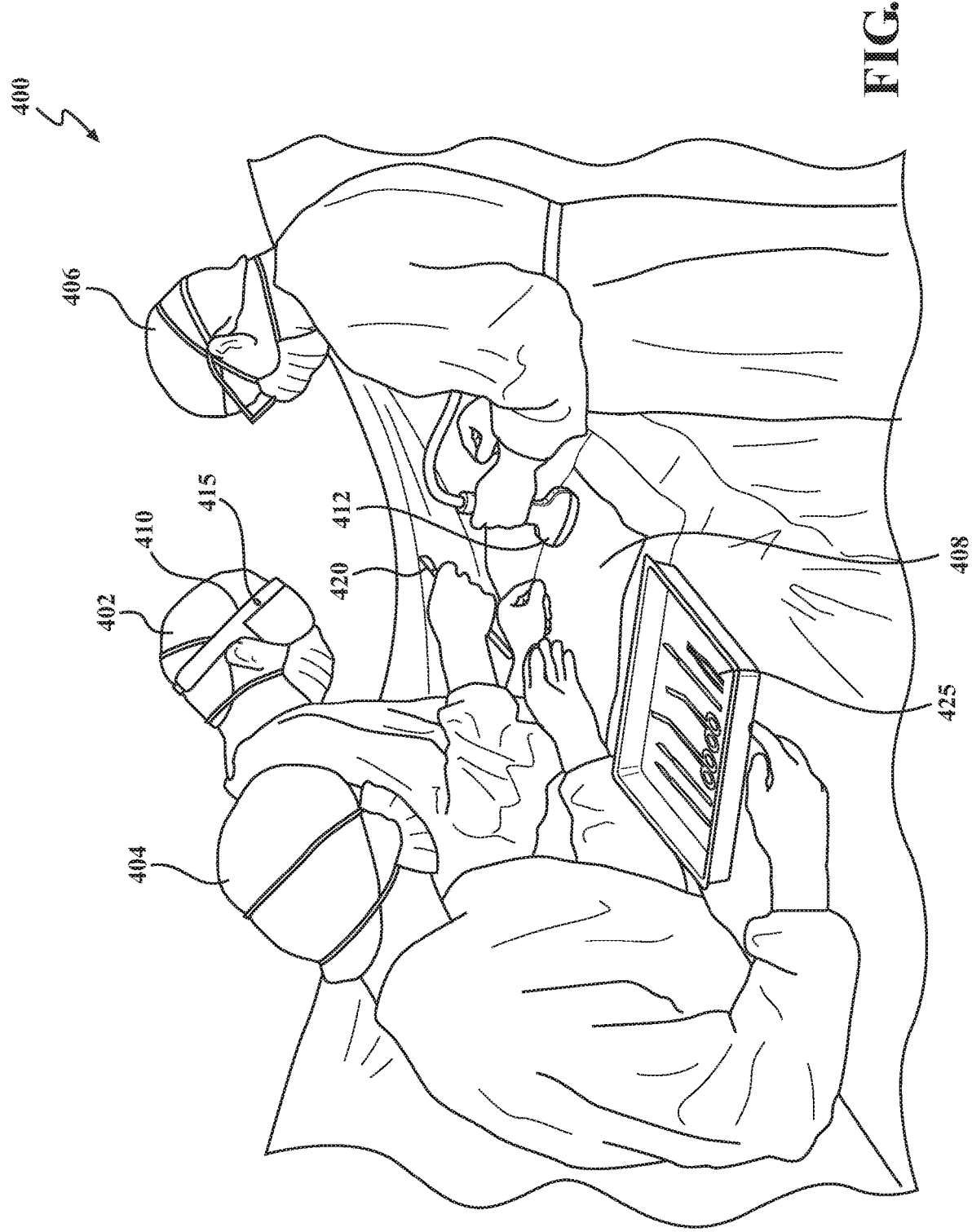
FIGS. 4A and 4B depict an operating procedure incorporating elements of the anatomical presentation system, according to embodiments described herein.
Figure 4B:
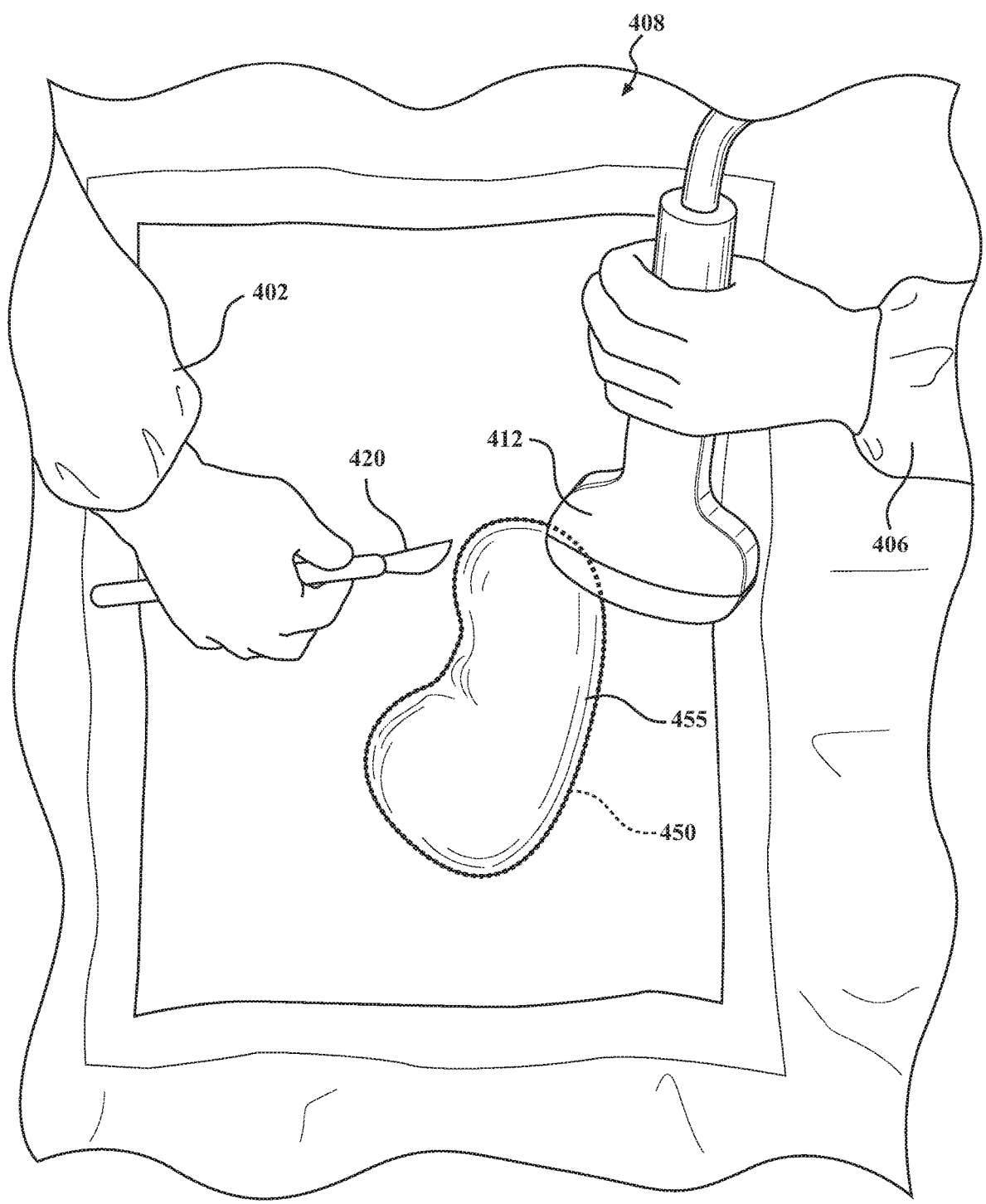

FIGS. 4A and 4B depict an operator in an operating room incorporating the anatomical presentation system 170, according to one embodiment. FIG. 4A depicts the operating room 400, having a physician 402, a technician 406, and an assistant 404 positioned over a subject 408. The physician 402 is depicted as wearing an AR display device 410 and holding a scalpel 420. The technician is holding an ultrasound device 412 over an anatomical structure 450, visible in FIG. 4B. The assistant 404 is positioned at the lower end of the subject 408, prepared to hand one or more objects 425, such as surgical implements, gauze, or others, to the physician 402, as requested or as necessary. The AR display device 410 can be substantially similar to the AR display device 150, described above with reference to FIG. 1. The AR display device 410 can present one or more images to the physician 402, such that the image in virtual space, appears to exist in real space from the point of view of the physician 402.

During the procedure, the physician 402 is preparing to remove a kidney from the subject 408. The technician 406 positions the ultrasound device 412, such that the acquisition module 220 of the anatomical presentation system 170 can collect the image data set 305. The acquisition module 220 can access information available in the imaging data 270 prior to or concurrently with receiving the image data set 305. The imaging data 270 can further include a representative model of the kidney, created as described with reference to FIG. 2. The representative model can be further modified using secondary imaging data 315, the image data set 305, or both. The secondary imaging data 315 can include imaging data from a variety of other sources, such as secondary imaging techniques, such that the representative model of the anatomical structure is personalized to the subject 408. As shown here, the technician 406 collects the image data set with the ultrasound device 412 on the kidney 450. The technician 406 can continually collect and update the image data set 305 using the ultrasound device 412, such that the image data set 305 of the anatomical structure is refined over time.

The acquisition module 220 further collects visual image data 310 using an image capture device 415. The image capture device 415 can be a camera, such as a video camera. The image capture device 415, as shown here, is located on the AR display device 410. The visual image data 310 can include image data about the subject 408, other people or objects in the operating room 400, or about the operating room 400 generally. Further, the visual image data 310 can be used by the coordination module 230 for both object recognition and orientation. As shown here, the acquisition module 220 collects visual image data 310 about the subject 408, the assistant 404, the objects 425, the technician 406, the ultrasound device 412, physician 402, and the scalpel 420. The image data set 305, the visual image data 310 and the secondary imaging data 315 are then stored as part of the imaging data 270, for use by the coordination module 230.

The visual image data 310 can then be used by the acquisition module 220 to determine the non-rigid deformation of one or more components of the subject 408. The acquisition module 220 receives input regarding the movement of the subject 408 as the ultrasound device 412 is moved. The acquisition module 220 further includes instructions to collect information from the ultrasound device 412 regarding at least the changes in the position of the anatomical structure 450 due to the movement of the ultrasound device 412. These changes, as viewed from the image data set 305 and the visual image data 310, are compared to the related time frames to determine the non-rigid deformation of the anatomical structure 450 as it exists within the subject 408. As shown here, the ultrasound device 412 is applied with slight pressure to the abdomen of the subject 408, which provides data regarding the non-rigid deformation, including beginning and final shape and elasticity, of the anatomical structure 450. The non-rigid deformation data 320 can then be stored as part of the imaging data 270.

The coordination module 230 includes instructions to receive the imaging data 270 and create one or more data sets to orient the image of the anatomical structure in real space. The data sets can include the operator perspective 330, the device pose data 335, and the image pose data 340. The operator perspective 330 is the perspective of the physician 402 and can be determined as described above with reference to FIG. 2. The AR display device 410 can use the eye position of the physician 402, the position of the image capture device 415, or other information to determine the perspective of the physician. As well, the coordination module 230 can determine the device pose data 335, which is the pose of the ultrasound device 412 in real space. The device pose data 335 gives information about the image data set, as we know the image data set is captured by the ultrasound device 412. As shown here, the operator perspective 330 is determined from the position of the image capture device 415, using estimates of the eye position based on the AR display device 410 position. The device pose data 335 is collected from one or more sensors located in the ultrasound device 412, as positioned on the subject 408.

Thus, the coordination module 230 can determine the image pose data 340 from the device pose data 335. The device pose data 335, along with the image data set 305 including collection times for said data, can then applied to determine the image pose data 340. As shown here, the device pose data 335 collects a first position above the anatomical structure 450. Based on the shape of the anatomical structure 450 at that point, the position of the anatomical structure 450 is determined, as compared to the ultrasound device 412. In determining the image pose data 340, the coordination module 230 can further include the operator perspective 330 to reduce processing requirements and better align the image pose data 340. The operator perspective 330, the device pose data 335, and the image pose data 340 can then be stored in the perspective data 260.

The visualization module 240 is more clearly displayed with reference to FIG. 4B. FIG. 4B depicts an AR view of the subject 408 with an anatomical structure image 455 superimposed over the anatomical structure 450 of the subject 408, according to embodiments herein. Shown here, the physician 402 has an arm extended over the subject 408 and is holding the scalpel 420, apparently preparing to cut into the abdomen of the subject 408. The technician 406 is also positioned over the subject 408 at the anatomical structure 450. The technician 406 is holding the ultrasound device 412 over the anatomical structure 450 collecting and/or updating the image data set 305. The anatomical structure image 455 is shown in virtual space as overlaid onto the subject 408 and in the position of the anatomical structure 450 from the perspective of the physician 402.

The visualization module 240 includes instructions to map a perspective pose of the anatomical structure image in virtual space onto the subject 408 in real space. The anatomical structure image 455 can be generated using at least the image data set. In this embodiment, the anatomical structure image 455 can either be a superposition of the ultrasound data or a modification of a representative model, as described above. In further embodiments, the anatomical structure image 455 can include secondary imaging data 315 and/or non-rigid deformation data. The secondary imaging data 315 can be incorporated into the representative model, such that the representative model can be more easily modified to present the anatomical structure image 455. Shown here, the secondary imaging data 415 has been retrieved and incorporated into one or more representative models. As such, the representative models are personalized to the subject 408. The image data set is compared to the representative models, and then the representative model is updated, modified, or otherwise made more representative of the anatomical structure 450, using the image data set 305, to produce the anatomical structure image 455.

The anatomical structure image is then presented to the physician 402 through the AR display device 410. As such, the physician sees the subject 408 in real-time, as augmented by, at least, the anatomical structure image 455. Before incision, the anatomical structure is not visible to the physician 402. Thus, the anatomical structure image 450 provides insight to the physician 402 as to the specific anatomy of the subject 408. In further embodiments, the visualization module 240 can remove other obstructions from the view of the physician 402. As the technician 406 collects the image data set 305 using the ultrasound device 412, both the technician 406 and the ultrasound device 412 can obstruct the view of the physician 402. The visualization module 240 can include instructions to render said obstruction transparent or invisible to the physician 402. As shown here, the visualization module 240 uses collected information from the visual image data 310 and the inventory of environmental objects collected by the acquisition module 220, to determine that the ultrasound device 412 and the technician 406 occlude the view of subject 408 by the physician 402.

The visualization module 240 can then use visual images from the perspective of the physician 402 and blend one or more areas of those visual images with the equivalent real space objects. This blended image is then presented to the physician 402 through the AR display device 410 to augment the view of the real world objects as being transparent. Shown here, the technician 406 and the ultrasound device 412 are seen as transparent by the physician 402, thus presenting a more clear view of the subject 408 and the anatomical structure image 455. In this way, the visualization module 240 provides a clear view of the subject 408, thus allowing for the physician 402 to focus on the surgical task, rather than obstructions.

Thus, the anatomical presentation system 170 provides the physician 402 with numerous benefits. The physician 402 can then see the anatomical structure 450, as presented through the anatomical structure image, prior to making a single incision and without invasive probes. Further, the anatomical presentation system 170 allows the physician 402 to see the subject 408 better by removing obstructions to view, thus making the physician 402 more capable of focusing on the subject 408. Finally, the physician 402 is receiving the information about the anatomical structure 450 directly in their field of view, thus preventing the constant distraction of looking up at a monitor. In this way, the anatomical presentation system 170 allows for a safer and more efficient operating room experience for both the physician 402 and the subject 408. Also, the ergonomic strain of working with eyes on the monitor and hands on the subject 408 is alleviated.

Figure 5:
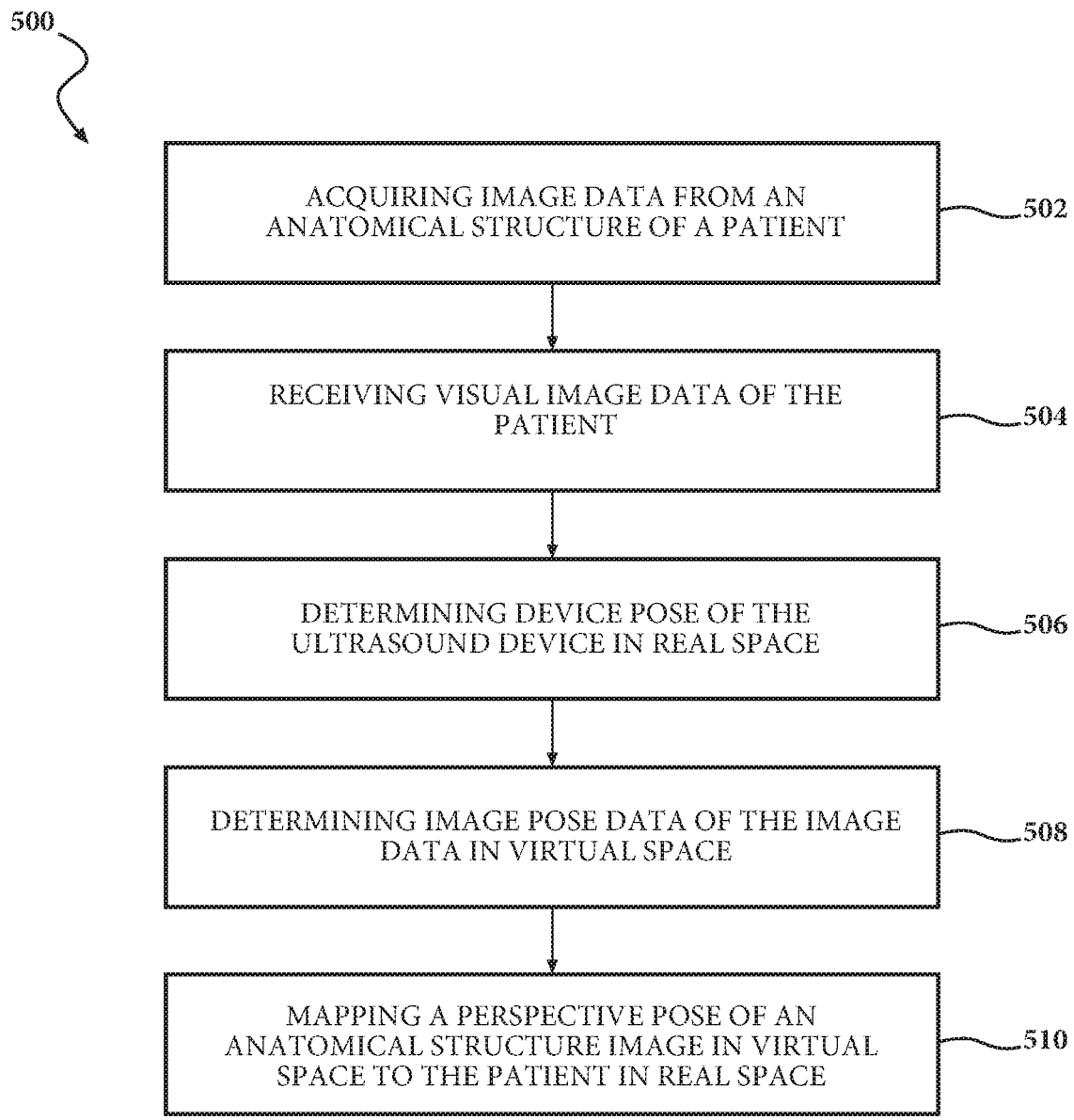
FIG. 5 is a block diagram of a method for real-time augmented visualization of anatomical features, according to embodiments described herein.

FIG. 5 is a block diagram of a method 500 for real-time augmented visualization of anatomical features, according to one or more embodiments herein. The method 500 collects an image data set for an anatomical structure. The image data set is then used to create or modify an anatomical structure image, which is then oriented to the environment and the subject. The anatomical structure image is then displayed to the operator as a virtual space overlay of real space, such that the anatomical structure image appears to exist in real space. In this way, the method 500 allows the operator to "see" the anatomical structure as they perform a procedure on a subject. As described herein, the method 500 can include acquiring an image data set, using an ultrasound device, from an anatomical structure of a subject, at 502. Then, the visual image data of the subject can be received, the visual image data including non-rigid deformation of the subject, at 504. The device pose data of the ultrasound device can be determined in real space, at 506. The image pose data of the image data set can be determined in virtual space, with relation to the ultrasound device, the subject, and an operator in real space, at 508. Then, a perspective pose of an image of at least a portion of the anatomical structure can be mapped in virtual space to the subject in real space, at 510.

The method 500 can begin with acquiring an image data set, using an ultrasound device, from an anatomical structure of a subject, at 502. The method 500 can include an operator applying the ultrasound device 130 to the subject. The one or more transducer elements then produce ultrasound and receive reflected ultrasound, producing an image data set for the anatomical structure that is targeted by the ultrasound device 130. In one or more embodiments, the ultrasound device 130 is moved by the operator or another party across the target surface of the subject, such that image data set is received from a variety of angles. The imaging data can include data that describes the position and orientation of the anatomical structure in three (3) dimensional space, commonly referred to as pose. The pose of the anatomical structure can be established with relation to a reference frame, thus establishing at least a portion of the orientation and boundaries applied to the virtual space. The image data set can include externally and internally derived data sets, such as ultrasound delivered through the skin, through one or more bodily openings, laparoscopically, or others.

The image data set, as collected using the method 500, can further comprise data that has been collected over a period of time. In one embodiment, the image data set can include ultrasound imaging data which has been collected over a variety of subject visits with the operator. In another embodiment, the imaging data can include secondary imaging data, the secondary imaging data being derived from one or more secondary detection events. The image data set can be collected with source agnostic information, such that information from different source sensors can be combined or used to augment the imaging data. The imaging data about the anatomical structure from the variety of time frames and origins can be oriented to one another using common points in virtual space to create a model of the anatomical structure.

The collection of image data from an anatomical structure can be performed as part of a system, such as the anatomical presentation system 170, described with reference to FIGS. 2 and 3. The anatomical presentation system 170 can include the acquisition module 220. The acquisition module 220 can include instructions that, when executed by the processor 210, cause the processor to acquire an image data set, using an ultrasound device, from an anatomical structure of a subject. The image data set can be substantially similar to the image data set, described with reference to FIGS. 2 and 3. The image data set can be collected using an ultrasound device in a substantially similar fashion to the image data set, described with reference to FIGS. 2 and 3. The image data set can be stored as part of the imaging data 270. The imaging data 270 can be stored in a database, such as the database 212, described with reference to FIG. 2.

Then, the visual image data of the subject can be received, the visual image data including non-rigid deformation of the subject, at 504. The visual image data includes information regarding the general shape, orientation and position of the subject and the environment such that the anatomical structure can be properly associated with the position of the subject. The visual image data can include reference information, such that the pose of objects in the environment. The visual image data can include still frame or video imaging received by one or more image capture devices. In one embodiment, the visual image data further includes data collected from a remote source, such as one or more image capture devices positioned as part of the infrastructure, such as on a wall in an operating room.

The visual image data can further include information regarding non-rigid deformation. The non-rigid deformation can be a movement of the skin and organs in response to pressure, such as applied by an operator through the ultrasound device, and can provide information regarding the present and original position of the anatomical structure. Further, the non-rigid deformation can provide information regarding the elasticity of the anatomical structure, related rigid or non-rigid structures, the permanency of the non-rigid deformation, or others. In further embodiments, the non-rigid deformation of the anatomical structure can provide information regarding possible future positions and deformations of the anatomical structure. As such, the method 500 can include applying that expected reproducibility to determine where and how an anatomical structure will move when a force is applied. Here, the forces applied, including quantity, origin and direction of the force, can be used to determine where and how the anatomical structure will move to when force is applied again. Thus, the level of non-rigid deformation or displacement of the anatomical structure can be related to an applied force for the purposes of future prediction.

The collection of visual image data and non-rigid deformation can be performed as part of a system, such as the anatomical presentation system 170, described with reference to FIGS. 2 and 3. The anatomical presentation system 170 can include the acquisition module 220. The acquisition module 220 can further include instructions to receive visual image data of the subject, the visual image data including non-rigid deformation of the subject. The visual image data can be substantially similar to the visual image data, described with reference to FIGS. 2 and 3. The visual image data can be collected using an image capture device in a substantially similar fashion to the visual image data, described with reference to FIGS. 2 and 3. Further, the non-rigid deformation data can be determined using the visual image data, the image data set, or combinations thereof. The visual image data can be stored as part of the imaging data 270. The imaging data 270 can be stored in a database, such as the database 212, described with reference to FIG. 2.

The device pose of the ultrasound device can be determined in real space using the device pose data, at 506. The device pose data is information regarding the real space pose of the ultrasound device. The device pose, as used herein, described in the sense of six degrees of freedom, which is described more clearly with reference to FIG. 2. As such, the device pose involves the position and orientation of the device with respect to a reference object or the environment generally. The device pose data can be determined by the method 500 based on external information sources, internal information sources, or combinations thereof. Internal information sources can include information from sources which are connect to or connected with the ultrasound device, such as derived from a gyroscope, an accelerometer, a magnetometer, a geolocation device (e.g., GPS, WiFi-based localization systems), or others. In one embodiment internal information, the device pose data is determined based on a magnetometer located within the ultrasound device. External information can include information from sources outside of or external to the ultrasound device 130. In one embodiment of external information, device pose data is determined based on one or more images produced by image capture devices, the image capture devices being positioned in known locations in the environment.

The determination of device pose can be performed as part of a system, such as the anatomical presentation system 170, described with reference to FIGS. 2 and 3. The anatomical presentation system 170 can include the coordination module 230. The coordination module 230 can include instructions that, when executed by the processor 210, cause the processor to determine device pose data of the ultrasound device 130 in real space. The device pose data can be substantially similar to the device pose data, described with reference to FIGS. 2 and 3. The device pose data can be collected using one or more internal or external sensors in a substantially similar fashion to the device pose data, described with reference to FIGS. 2 and 3. The device pose data can be stored as part of the perspective data 260. The perspective data 260 can be stored in a database, such as the database 212, described with reference to FIG. 2.

The image pose data of the image data set can be determined in virtual space, with relation to the ultrasound device, the subject, and an operator in real space, at 508. The image pose data is information regarding the pose of the image of the anatomical structure in virtual space. In one or more embodiments, the image pose data can be determined by the method 500 using the position and/or pose data from environmental objects, such as the device pose data described above with reference to the ultrasound device. In further embodiments, the image pose data can be determined at least in part based on the pose of the subject. The image pose data can include translations, positional, and rotational data regarding the anatomical structure. Further, the image pose data can include information regarding the non-rigid deformation of the anatomical structure, either as detected or as anticipated based on predictive information described above. The image pose data can include data derived from multiple sources, such as previous data collected regarding the anatomical structure, accumulated data regarding equivalent anatomical structures in other subjects, or others.

The method 500 can optionally further include determining operator perspective. The operator perspective can be determined from a variety of sources, such as the operator eye position, the position of the image capture device on the AR display device 150, or others. In one embodiment, the method 500 can use the operator eye position to determine the perspective of the operator. The operator eye position can be determined by a variety of techniques, including one or more image capture devices directed at the eyes. The operator eye position can include determination of gaze, depth perception of the operator, or other factors that can affect the operator's ability to view one or more objects. The operator eye position can be continuously determined, such that changes in the position of the AR display device 150 are accounted for, and the presentation of one or more images is not affected.

The determination of image pose data and the operator perspective can be performed as part of a system, such as the anatomical presentation system 170, described with reference to FIGS. 2 and 3. The anatomical presentation system 170 can include the coordination module 230. The coordination module 230 can further include instructions to determine image pose data of the image data set and the operator perspective. The image pose data and the operator perspective can be substantially similar to the image pose data and the operator perspective, described with reference to FIGS. 2 and 3. The image pose data and the operator perspective can be determined in a substantially similar manner as described with reference to FIGS. 2 and 3. The image pose data and the operator perspective can be stored as part of the perspective data 260. The perspective data 260 can be stored in a database, such as the database 212, described with reference to FIG. 2.

Then, a perspective pose of an image of at least a portion of the anatomical structure can be mapped in virtual space to the subject in real space, at 510. The anatomical structure image, as presented to the operator in virtual space, can be overlaid onto the anatomical structure, as it exists in the subject in real space. In one embodiment, the anatomical structure image can be used to show otherwise obstructed angles of the anatomical structure. In another embodiment, the anatomical structure image can include cutaway images of adjacent or occluding anatomical structures, to orient the operator with regards to positioning of the anatomical structure in the subject.

The operator perspective can then be applied by the method 500 to determine the perspective pose of the image of the anatomical structure. Using the image pose data, the device pose data, the operator perspective, and other positioning data, the method 500 can provide the operator an image of the anatomical structure with a perspective pose of the anatomical structure. In one or more embodiments, the perspective pose can change, in real-time, with the perspective of the operator. The method 500 can further include updated information on the operator perspective. The imaging data, including the image data set, can then be accessed to provide the perspective pose of the anatomical structure as it changes over a period of time.

The imaging data can include two dimensional and three dimensional imaging data regarding one or more perspectives of the anatomical structure. The two dimensional and three dimensional imaging data can include data as received from the ultrasound device or other imaging devices. In one embodiment, the imaging data can further include a representative model. In one embodiment, the image data set is applied by the method 500 to modify the representative model of the anatomical structure. Further, the image data set can then be applied to modify the representative model in real-time. The representative model can be derived from a variety of model sources, as described above with reference to FIG. 2. As such, the imaging data 270, including the image data set, can be applied to create or update the representative model source for one or more anatomical structures. Various data incorporation techniques can be used to incorporate the imaging data 270 to produce the representative model, such as Bayesian filtering, feature detection and fitting, spatiotemporal 3D reconstruction, or others.

The mapping of the perspective pose of an anatomical structure in virtual space can be performed as part of a system, such as the anatomical presentation system 170, described with reference to FIGS. 2 and 3. The anatomical presentation system 170 can include the visualization module 240. The visualization module 240 can include instructions that, when executed by the processor 210, cause the processor to map a perspective pose of an anatomical structure image in virtual space to the subject in real space. The perspective pose can be substantially similar to the perspective pose, described with reference to FIGS. 2 and 3. The perspective pose can be determined in a substantially similar fashion to the perspective pose, described with reference to FIGS. 2 and 3. The perspective pose can be stored as part of the imaging data 270 or presented to the operator through the AR display device 150, described with reference to FIG. 2.

Optionally, the method 500 can further include analyzing the image data set to recognize the anatomical structure for selection of a representative model. The analysis can include monitoring the image data set for one or more anatomical structures in the subject and compare to existing representative models. In this way, the representative models for anatomical structure can be uniquely identified and differentiated from other anatomical structures. This unique identification is converted to recognition data, which can be stored, processed or otherwise maintained. Once the anatomical structure is uniquely identified, the anatomical structure can be associated with a representative model having a unique identifier. The unique identifier can be preexisting, such as when the anatomical structure has been detected before, or the unique identifier can be created in response to a new anatomical structure. The unique identifier can be stored along with one or more 3D objects or representative models which can be associated with the anatomical structure. If an anatomical structure is detected that has already received a unique identifier, the anatomical structure can then be associated to a preexisting representative model. The method 500 can further include manually associating the representative model or the identifier to a subject through user input. One or more data points from the image data set can be incorporated into the representative model, such that the representative model better reflects the anatomical structure.

As well, the model sources can be personalized to a specific subject. As differentiated from a subject specific presentation of the anatomical structure, using more general models for adaptation, subject models can be generated that specifically address the subject's unique physiology at one or more anatomical structures. In embodiments described herein, imaging data can be collected from a variety of points of view over a period of time. This imaging data can be applied to modify or create a subject specific 3D model, unique to the physiology of the subject. The subject specific model can then be referenced during scanning, modified using the image data set, and presented to the operator during a procedure. In this way, the model sources will require less real-time modification while providing a high level of detail both on structures that can be currently visualized and those that are not visible based on the current ultrasound placement.

In further embodiments, the method 500 can include incorporating modification of the anatomical structure image based on one or more actions of the operator in real space. Modifications of the anatomical structure image can include incorporation of surgical procedures as they are performed. In one example, an incision in the anatomical structure by the operator can be detected and depicted in real-time in the anatomical structure image in virtual space. In another embodiment, the modifications can include incorporation of one or more gestures, such as one or more hand movements or audible commands which manipulate the view or pose of the anatomical structure image. In further embodiments, the anatomical structure image can be adjusted based on detected eye position and focus of the operator. Additionally, the modifications can include creating safety boundaries around delicate structures, such as an artery or organ. Further, the visualization module 240 can decipher the one or more pre-operative images to define and label structures, organs, anatomical geometries, vessels, tissue planes, orientation, and other similar information.

In embodiments which include multiple operators, the method 500 can determine and present multiple perspective poses of the anatomical structure image. In one embodiment, the coordination module 230 can determine the operator perspective for each of the one or more operators. The operator perspective can then be applied to determine the perspective pose of the anatomical structure image for each operator. The method 500 can then present the perspective pose of the anatomical structure image to the one or more operators in real-time. In further embodiments, the one or more operators can interact with the anatomical structure or the anatomical structure image, and this interaction can be shared with the other operators as part of their respective anatomical structure image, as overlaid on the subject.

In yet further embodiments, the method 500 can render one or more obstructions transparent or invisible to the operator. The method 500 can exclude or render transparent objects which are not part of the operator's desired view, including other parties in the operating room, or tools in use by those parties. In this embodiment, the method 500 can include recognizing the one or more object in the operating room. The object recognition can be accomplished using the comparison to 3D models, appearance based methods, feature based methods, genetic algorithms, or others. The recognized objects can then be associated with one or more parties (e.g., the operators or others in the view range).

The method 500 can then present an image overlay, in virtual space, of the space behind the object, to create the illusion of object transparency or object invisibility for the operator. The method 500 can compare images taken over a period of time to collect data about the operator's view of the room both with the object (the "object view") and without the object (the "displaced view"). The portions of the displaced view can then be blended or overlayed with the object from the object view, thus rendering the object translucent, transparent, or invisible from the perspective of the operator. The image overlay can be updated in real-time such that the image follows the object or the person.

Detailed embodiments are disclosed herein. However, it is to be understood that the disclosed embodiments are intended only as examples. Therefore, specific structural and functional details disclosed herein are not to be interpreted as limiting, but merely as a basis for the claims and as a representative basis for teaching one skilled in the art to variously employ the aspects herein in virtually any appropriately detailed structure. Further, the terms and phrases used herein are not intended to be limiting but rather to provide an understandable description of possible implementations. Various embodiments are shown in FIGS. 1-5, but the embodiments are not limited to the illustrated structure or application.

The flowcharts and block diagrams in the figures illustrate the architecture, functionality, and operation of possible embodiments of systems, methods, and computer program products according to various embodiments. In this regard, each block in the flowcharts or block diagrams can represent a module, segment, or portion of code, which comprises one or more executable instructions for implementing the specified logical function(s). It should also be noted that, in some alternative embodiments, the functions noted in the block can occur out of the order noted in the figures. For example, two blocks shown in succession can, in fact, be executed substantially concurrently, or the blocks can sometimes be executed in the reverse order, depending upon the functionality involved.

The systems, components and/or methods described above can be realized in hardware or a combination of hardware and software and can be realized in a centralized fashion in one processing system or in a distributed fashion where different elements are spread across several interconnected processing systems. Any kind of processing system or other apparatus adapted for carrying out the methods described herein is suited. A typical combination of hardware and software can be a processing system with computer-usable program code that, when being loaded and executed, controls the processing system such that it carries out the methods described herein. The systems, components and/or methods also can be embedded in a computer-readable storage, such as a computer program product or other data programs storage device, readable by a machine, tangibly embodying a program of instructions executable by the machine to perform methods and methods described herein. These elements also can be embedded in an application product which comprises all the features enabling the embodiment of the methods described herein and, which when loaded in a processing system, is able to carry out these methods.

Furthermore, arrangements described herein can take the form of a computer program product embodied in one or more computer-readable media having computer-readable program code embodied or embedded, such as stored thereon. Any combination of one or more computer-readable media can be utilized. The computer-readable medium can be a computer-readable signal medium or a computer-readable storage medium. The phrase "computer-readable storage medium" means a non-transitory storage medium. A computer-readable storage medium can be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: an electrical connection having one or more wires, a portable computer diskette, a hard disk drive (HDD), a solid state drive (SSD), a RAM, a ROM, an EPROM or Flash memory, an optical fiber, a portable compact disc read-only memory (CD-ROM), a digital versatile disc (DVD), an optical storage device, a magnetic storage device, or any suitable combination of the foregoing. In the context of this document, a computer-readable storage medium can be any tangible medium that can contain, or store a program for use by or in connection with an instruction execution system, apparatus, or device.

Program code embodied on a computer-readable medium can be transmitted using any appropriate medium, including but not limited to wireless, wireline, optical fiber, cable, RF, etc., or any suitable combination of the foregoing. Computer program code for carrying out operations for aspects of the present arrangements can be written in any combination of one or more programming languages, including an object-oriented programming language such as Java™, Smalltalk, C++ or the like and conventional procedural programming languages, such as the "C" programming language or similar programming languages. The program code can execute entirely on the operator's computer, partly on the operator's computer, as a stand-alone software package, partly on the operator's computer and partly on a remote computer, or entirely on the remote computer or server. In the latter scenario, the remote computer can be connected to the operator's computer through any type of network, including a local area network (LAN) or a wide area network (WAN), or the connection can be made to an external computer (for example, through the Internet using an Internet Service Provider).

The terms "a" and "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The phrase "at least one of . . . and . . . " as used herein refers to and encompasses any and all possible combinations of one or more of the associated listed items. As an example, the phrase "at least one of A, B and C" includes A only, B only, C only, or any combination thereof (e.g., AB, AC, BC or ABC).

While the foregoing is directed to embodiments of the disclosed devices, systems, and methods, other and further embodiments of the disclosed devices, systems, and methods can be devised without departing from the basic scope thereof. The scope thereof is determined by the claims that follow.

What is claimed is:

1. An anatomical presentation system for real-time augmented visualization of anatomical features, comprising: one or more processors; and
a memory communicably coupled to the one or more processors and storing:
an acquisition module comprising instructions that when executed by the one or more processors cause the one or more processors to acquire image data, using an ultrasound device, from an anatomical structure of a subject and to receive visual image data of the subject, the image data including deformation data for the anatomical structure, the deformation data being data collected about the mobility of the anatomical structure in response to one or more forces;
a coordination module comprising instructions that when executed by the one or more processors cause the one or more processors to determine a device pose of the ultrasound device in real space, and to determine image pose data of the image data and the visual image data in virtual space, with relation to the device pose of the ultrasound device, the subject, and an operator in real space; and
a visualization module comprising instructions that when executed by the one or more processors cause the one or more processors to map a perspective pose of an anatomical structure image in virtual space to the subject in real space, the anatomical structure image being a visual representation of the anatomical structure constructed from at least the image data, the visual image data and the image pose data, the anatomical structure image incorporating one or more visualizations of the non-rigid deformation of the anatomical structure, in response to the one or more forces, as derived from the deformation data.

2. The anatomical presentation system of claim 1, wherein the acquisition module further comprises instructions to collect subject deformation data for the subject, and to predict one or more deformations of the anatomical structure using the subject deformation data.

3. The anatomical presentation system of claim 2, wherein the acquisition module further comprises, instructions to predict one or more deformations of a secondary structure in the subject, based on the predicted deformations of the anatomical structure.

4. The anatomical presentation system of claim 1, wherein the image data comprises a first image data collected at a first period of time about the anatomical structure and real-time image data concurrently collected with the visual image data about the anatomical structure, the first, image data and the real-time image data being merged to produce the anatomical structure image.

5. The anatomical presentation system of claim 1, wherein the image data comprises an ultrasound image data and secondary image data collected using, a secondary imaging technique.

6. The anatomical presentation system of claim 5, wherein the coordination module further comprises instructions to produce a hybrid data set from the ultrasound image data and the secondary image data, the hybrid data set being used to produce the anatomical structure image.

7. The anatomical presentation system of claim 1, wherein the visualization module further comprises instructions to render obstructing objects transparent to the operator.

8. A non-transitory computer-readable medium for real-time augmented visualization of anatomical features and storing instructions that when executed by one or more processors cause the one or more processors to:
acquire image data, using an ultrasound device, from an anatomical structure of a subject;

receive visual image data of the subject, the image data including deformation data for the anatomical structure, the deformation data being data collected about the mobility of the anatomical structure in response to one or more forces;

determine device pose of the ultrasound device in real space;

determine image pose data of the image data and the visual image data in virtual space, with relation to the device pose of the ultrasound device, the subject, and an operator in real space; and map a perspective pose of an anatomical structure image in virtual space to the subject in real space, the anatomical structure image being a visual representation of the anatomical structure constructed from at least the image data, the visual image data, and the image pose data, the anatomical structure image incorporating one or more visualizations of the non-rigid deformation of the anatomical structure, in response to the one or more forces, as derived from the deformation data.

9. The non-transitory computer-readable medium of claim 8, further comprising instructions to collect subject deformation data for the subject, and predict one or more deformations of the anatomical structure using the subject deformation data.

10. The non-transitory computer-readable medium of claim 9, further comprising instructions to predict one or more deformations of a secondary structure in the subject, based on the predicted deformations of the anatomical structure.

11. The non-transitory computer-readable medium of claim 8, wherein the image data comprises a first image data collected at a first period of time about the anatomical structure and second image data concurrently collected with the visual image data about the anatomical structure, the first image data and the second image data being merged to produce the anatomical structure image.

12. The non-transitory computer-readable medium of claim 8, wherein the image data comprises an ultrasound image data and secondary image data collected using a secondary imaging technique.

13. The non-transitory computer-readable medium of claim 12, further comprising instructions to produce a hybrid data set from the ultrasound image data and the secondary image data, the hybrid, data set being used to produce the anatomical structure image.

14. The non-transitory computer-readable medium of claim 8, further comprising instructions to render obstructing objects transparent to the operator.

15. A method for real-time augmented visualization of anatomical features, comprising:

acquiring image data, using an ultrasound device, from an anatomical structure of a subject;

receiving visual image data of the subject, the image data including deformation data for the anatomical structure, the deformation data being data collected about the mobility of the anatomical structure in response to one or more forces;

determining device pose of the ultrasound device in real space;

determining image pose data of the image data and the visual image data in virtual space, with relation to the device pose of the ultrasound device, the subject, and an operator in real space; and mapping a perspective pose of an anatomical structure image in virtual space to the subject in real space, the anatomical structure image being a visual representation of the anatomical structure constructed from at least the image data, the visual image data, and the image pose data, the anatomical structure image incorporating one or more visualizations of the non-rigid deformation of the anatomical structure, in response to the one or more forces, as derived from the deformation data.

16. The method of claim 15, further comprising:
collectins subject deformation data for the subject; and
predicting one or more deformations of the anatomical structure using the subject deformation data.

17. The method of claim 15, further comprising predicting, one or more deformations of a secondary structure in the subject, based on the predicted deformations of the anatomical structure.

18. The method of claim 15, wherein the image data comprises a first image data collected at a first period of time about the anatomical structure and second image data concurrently collected with the visual image data about the anatomical structure, the first image data and the second image data being merged to produce the anatomical structure image.

19. The method of claim 15, wherein the image data comprises an ultrasound image data and secondary image data collected using a secondary imaging technique, and further comprising producing a hybrid data set from the ultrasound image data and the secondary image data, the hybrid data set being used to produce the anatomical structure image.

20. The method of claim 15, further comprising rendering obstructing objects transparent to the operator.

* * * * *